United States Patent [19]

Campbell et al.

[11] Patent Number: 4,487,988

[45] Date of Patent: Dec. 11, 1984

[54] NITRATION OF ORGANIC COMPOUNDS

[75] Inventors: Ian M. Campbell; Donald L. Baulch, both of Leeds; Jonathan M. Chappel, Spalding, all of England

[73] Assignee: Interox Chemicals Limited, England

[21] Appl. No.: 489,466

[22] Filed: Apr. 28, 1983

[30] Foreign Application Priority Data

Sep. 21, 1982 [GB] United Kingdom ............... 8226938

[51] Int. Cl.$^3$ ............................................. C07C 76/02
[52] U.S. Cl. ................................. 568/943; 260/466; 260/467; 568/924; 568/947
[58] Field of Search ............... 568/943, 944, 947, 948, 568/924; 260/466, 467

[56] References Cited

U.S. PATENT DOCUMENTS 3,966,411 6/1976 Ross et al. ........................... 436/149
4,329,522 5/1982 Gilbert et al. ........................ 149/92

OTHER PUBLICATIONS

Urbanski, Chemistry and Technology of Explosives, vol. I, The MacMillan Co., New York, 1964, pp. 120, 121, 136 and 137, (TP 270 U7).

*Primary Examiner*—Leland A. Sebastian
*Attorney, Agent, or Firm*—Larson & Taylor

[57] ABSTRACT

Organic nitrogen compounds are formed in the vapor phase by organic radical formation by reaction of an organic compound, suitably an alkane, with hydroxyl radicals derived from the reaction between hydrogen peroxide and nitrogen dioxide and the nitration of the organic radicals, suitably with nitrogen dioxide. The process is conducted using a molecular oxygen additive which directs the reaction towards the formation of the nitrate corresponding to the organic compound which may predominate in the organic reaction products.

13 Claims, No Drawings

NITRATION OF ORGANIC COMPOUNDS

This invention relates to the nitration of organic compounds and nitrogen compounds so produced. The term "nitration" is used to mean, in general sense, the inclusion of nitrogen containing groups in organic compounds.

The high temperature non-photolytic vapour phase nitration of hydrocarbons by means of nitric acid or nitrogen dioxide is referred to in the Encyclopaedia of Chemical Technology (Kirk-Othmer) Ed 2 Vol 13 page 790. That reference discloses that, when nitrogen dioxide is used as the nitrating agent, nitration occurs at temperatures of from about 200° C. to 450° C. Pressures of 1 to 12 atmospheres (1 to $12 \times 101325$ Nm$^{-2}$) may be used although pressures above atmospheric are used commercially. At lower temperatures, within the disclosed range, a residence time of up to several minutes is required to obtain a significant degree of reaction and, even then, the conversion of nitrogen dioxide to the desired organic nitrogen compounds is significantly less than that obtained using nitric acid. An alternative process for the vapour phase nitration of hydrocarbons using nitrogen dioxide could therefore be of considerable commercial benefit in view of the above stated disadvantages.

A theoretical study of the reactivity of hydroxyl radicals towards a reactive substrate (butane) to produce a radical of the substrate (butyl) using the reaction between hydrogen peroxide and nitrogen dioxide as a source of hydroxyl radicals has been published in the Journal of the Chemical Society (Faraday Transactions I) 1975 Vol 71 pages 867 to 874. In that study the reacton between the hydroxyl radical and the substrate was essentially conducted in the presence of an excess of carbon monoxide, within the range

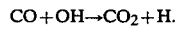

$$\frac{[\text{butane}]}{[\text{CO}]} = 0.005 \text{ to } 0.08 \text{ which}$$

carbon monoxide competed with the substrate for the hydroxyl radicals by virtue of the reaction $$CO + OH \rightarrow CO_2 + H.$$

The decrease in the yield of carbon dioxide in the presence of the substrate gives a measure of the reactivity of the substrate with hydroxyl radicals in comparison with that of carbon monoxide. Since the reactivity of carbon monoxide is known an estimate of the reactivity of the substrate with hydroxyl radicals may be derived. The theoretical possibility that some of the radicals of substrate could combine with nitrogen dioxide to give a low concentration of the corresponding nitrite is envisaged although no such product was actually confirmed to be present.

According to the present invention, the reaction between hydrogen peroxide and nitrogen dioxide may be used, in the absence of CO, as a source of hydroxyl radicals for organic synthesis. Such a reaction may be used in a practical vapour phase process for the nitration of organic compounds. The process may be operated non-photolytically at or near ambient temperature and at ambient or reduced pressure using relatively short residence times. By 'non-photolytic' is meant a reaction in which no photon energy is used to break a bond. Only thermal reactions are involved herein which can achieve a higher energy efficiency overall than a photolytic process.

Further, according to the present invention the composition of the product may be directed substantially wholly, or to a desired extent, to the nitrate with a decreased quantity of nitrocompound and nitrate by the use of an additive comprising molecular oxygen which additive would have been expected to direct a nitration reaction to an increased proportion of nitrocompound. The nitrate so produced usually comprises a mixture of the possible isomers.

According to a particular aspect thereof the present invention provides a process for the nitration of one or more organic compounds comprising reacting, in the vapour phase, the one or more organic compounds with a nitrating agent, the process being characterised in that radicals of the one or more organic compounds are produced for nitration by reacting hydrogen peroxide vapour and nitrogen dioxide in the presence of a solid surface to produce hydroxyl radicals and reacting the hydroxyl radicals with a vapour of a reactive substrate mainly comprising the one or more organic compounds by forming a mixture containing the hydroxyl radicals and the vapour of the reactive substrate or containing hydrogen peroxide vapour and nitrogen dioxide, as hydroxyl radical precursors, in the presence of the solid surface, and the vapour of the reactive substrate and in that the radicals so produced are contacted with the nitrating agent and in that an additive comprising molecular oxygen is used. The terminology "mainly comprising the one or more organic compounds" is used to limit to a minor proportion, that is to less than 50% on a molar basis, the presence of any other material and in particular CO, which is capable of reacting with the hydroxyl radicals in competition with the organic compound, thereby reducing the overall yield based on the quantity of hydrogen peroxide used. Preferably the minor proportion is less than 20%, particularly, preferably not more than 10%, in a molar basis.

The nitration of the organic radicals may be conducted using any suitable nitrating agent. However, it is found particularly advantageous for the nitration to be conducted "in situ" in a single process stage in the radical production reaction medium and in this case it is preferred that the nitrating agent is nitrogen dioxide, suitably included as an excess over that required to produce the hydroxyl radicals.

Subject to the consideration that the organic compound, to be suitable for use as a substrate in the present invention, must be vaporisable at the pressure and temperature employed and reactive with hydroxyl radicals, a wide variety of organic compounds may be employed as the substrate. Examples of aliphatic compounds from which suitable substrates may be selected are alcohols, ketones, aldehydes or ethers, or preferably, alkanes. Aromatic compounds may be found to be suitable as may aromatic derivatives of aliphatic compounds. The presence on the organic compound of inorganic substituents which do not interfere with the process nor the suitability of the organic compound is not excluded.

The alkanes which may be straight or branched chain and, preferably contain from 1 to 20 carbon atoms and particularly preferably from 1 to 10 carbon atoms. Examples of particularly suitable alkanes are methane, ethane, n-butane and n-pentane.

It is found that, to increase the yield of hydroxyl radicals, the reaction between the hydrogen peroxide and the nitrogen dioxide to form the hydroxyl radicals is advantageously conducted in the presence of a solid surface suitable to encourage the adsorption of the hydrogen peroxide vapour thereon.

Preferably, such a surface is an acidic solid surface is used, such surface being found to have a catalytic effect on the reaction. Suitable acidic solid surfaces may be composed of an acid which may be a solid acid or a liquid or gaseous acid adsorbed on an inert surface. Preferably the acidic solid surface so provided by a solid inorganic acid such as, for example, boric acid or fused phosphoric acid. Alternatively, the acidic solid surface may be composed of or comprise one or more acidic oxides or mixed oxides, such as alumina, or a silica-aluminia compound such as a zeolite or other silica containing acidic mixed oxide. In a paper in Industrial and Engineering Chemistry Nov. 1974 pages 2564 to 2573 there is postulated a test whereby acidity in oxides or mixed oxides may be detected. The test involves the measurement of the quantity of KOH which will react with a given weight of the oxide as indicated by titration with 0.1N HCL using phenolphthalein as indicator. The said test may be as a criterion for the selection of acidic oxides or mixed oxides for use according to this invention in which event, preferably, the acidity of the acidic solid surface material is at least 1.0 particularly preferably at least 2 meHOH/g. Suitably, the material providing the acidic surface is coated onto a suitable support such as a refractory reactor packing material to enchance the surface area available to the hydrogen peroxide and/or onto the reactor itself. Such coating may suitably be by deposition from a solution of an acidic material, or of from a reaction mixture containing the precursors thereof, or by applying the acidic material as such directly to the surface. A particularly suitable combination of solid material and support is boric acid coated onto glass.

Besides acidity and suitability for adsorption of hydrogen peroxide thereon, various other features contribute to suitability in the material providing the solid surface. Such features include a lack of undue reactivity with nitric acid or water formed in the course of the process and a lack of undue solubility in water and any organic materials, such as excess substrate, which may be present to the extent that the acidic solid surfae should not the dissolved away. Such features are possessed by the materials disclosed above.

Preferably the invention is performed in a single composite reaction stage hydrogen peroxide, alkane and nitrogen dioxide being introduced into one end of a reactor, for example a tube or packed flow reactor, through which a flow of the resulting gas mixture, comprising reactants, reaction products and diluent if used, is maintained. The reactants and diluent may be introduced into the reactor separately although it is found to be particularly suitable to introduce the organic compound and nitrogen dioxide as one gaseous flow and the hydrogen peroxide and diluent, if any, as another gaseous flow.

Preferably the reactant streams are introduced axially into the reactor. Particularly preferably the hydrogen peroxide stream is introduced into an established stream of the organic compound and nitrogen dioxide. Preferably, the said introduction is co-current to and axially with the stream of organic compound and nitrogen dioxide. As a result, the mixed stream of reactants and diluent flow progressively along the reactor towards the exit while the introduction of the organic compound is in operation. In the single stage type of process it is preferred to use a greater concentration of organic compound than of nitrogen dioxide so as to reduce the proportion of hydroxyl radicals consumed by reaction with the nitrogen dioxide. Very suitably, the ratio of the concentration of the organic compound to that of the nitrogen dioxide is at least 10 to 1 for example possibly, up to 100 to 1 or even up to 500:1 or even greater.

When operating the process in a single stage the concentration of nitrogen dioxide is, preferably, greater than that of the hydrogen peroxide. Preferably, the ratio of the concentration of the nitrogen dioxide to that of the hydrogen peroxide is at least 10 to 1, for example possibly up to 50:1 or even greater.

Examples of suitable concentrations for the organic compound, the nitrogen dioxide and the hydrogen peroxide are respectively from 0.2 to $15 \times 10^{-2}$ for example $1.6 \times 10^{-2}$ mol $dm^{-3}$, 0.5 to $50 \times 10^{-5}$ for example $5 \times 10^{-5}$ mol $dm^{-3}$ and 0.2 to $25 \times 10^{-6}$ for example $2.3 \times 10^{-6}$ mol $dm^{-3}$.

Whatever the method used to bring the reactants into contact the process is operated at a temperature, of preferably, less than 200° C. and, particularly preferably, less than 100° C. Very suitably the process is operated at a temperature of at least 0° C. Operation at superatmospheric pressure is not excluded from the scope of the invention although, preferably, a pressure of from $10^3 Nm^{-2}$ to $93.3 \times 10^3 Nm^{-2}$ may be used.

A gaseous diluent inert to the reaction may be used as required to adjust the concentrations of the reactants. Suitably the gaseous diluent is an inert gas or nitrogen. The use of additives to facilitate the operation of the nitration process is not excluded as is apparent from the development of the invention described below.

The composition of the final product tends to relate to the quantity of oxygen additive used. Preferably the oxygen additive is present in at least 1.75%, particularly preferably at least 5% and very suitably at least 6% as a proportion of the entire gaseous input into the reaction on a molar basis. There is no upper limit although for practical considerations the oxygen additive may suitably be present in less than 50% and preferably less than 45% on the same volume basis. It may be desired to control the composition of the product at some point short of the maximum production of alkyl nitrates in which case an appropriate quantity of oxygen between, for example, 1% and 10% may be seclected on the same molar basis.

The product of the invention as above specifically described tends to be a mixture of two or all of nitrocompounds ($RNO_2$), nitrates ($RONO_2$) and nitrites ($RONO$), where R is the radical of the organic compound used as substrate with the nitrate in preponderance and usually contains a residual quantity of the organic substrate where, as is preferred, an excess thereof has been used.

It is a feature of the invention that the product may be condensed from the gas phase and directly used. One application for the product of the present invention is as an additive to fuel mixtures for internal combustion engines whether of the spark ignition or of the compression ignition type and the present invention therefore futher provides such a fuel additive and a process for operating an internal combustion engine utilising such a fuel additive. Alternatively, the residual organic substrate or some of it may be removed for example by distillation and, if desired, the components of the mixture separated.

The invention will now be illustrated by means of Example 1 to 12.

EXAMPLES 1 TO 12

A tube reactor of glass having a coating of boric acid on the inner wall surface and painted black on the external surface to exclude light was used. The reactor was equipped with a cooling jacket, an inlet axially positioned at one end, and an inlet conduit entering the reactor radially shortly downstream of the first mentioned inlet but bent in the downstream direction at its end to coincide with the reactor axis, and an outlet at the end distant from the inlet. Additionally the reactor was equipped with means to control and monitor the pressure therein.

In operation a mixture of vapour of the organic compound to be nitrated, oxygen if present, and $NO_2$ was passed into the reactor through the axial inlet and a mixture of hydrogen peroxide vapour and nitrogen was passed into the resulting stream of this vapour mixture through the inlet conduit. The gases were passed through the reactor, removed through the outlet and passed to a trap and analysis system. The gases resulting from the reaction were examined by gas chromatography. The individual components of the mixture were identified by comparison of their retention times with pure compounds. The concentrations of the individual components of the mixture were derived by comparing the various peak areas with a calibration graph constructed using known concentrations of the components.

A series of experiments (Examples 1-12) was conducted using a reactor tube pressure of $39.9 \times 10^3 NM^{-2}$ and a temperature of $298 +/- 1°$ K. The organic compound to be nitrated was normal pentane. In these experiments the concentration of $NO_2$ was $5.5 \times 10^{-5}$ mol $dm^{-3}$ the concentration of normal pentane was $1.3 \times 10^{-3}$ mol $dm^{-3}$ the concentration of hydrogen peroxide was $3.0 \times 10^{-6}$ mol $dm^{-3}$ and the concentration of nitrogen was $1.48 \times 10^{-2}$-$O_2$ mol $dm^{-3}$. The quantity of oxygen was varied between 0 in Example 1 (comparative) to $72.4 \times 10^{-4}$ mol $dm^{-3}$. The flow rate of the total reactants was $6.5 \times 10^{-5}$ mol per second.

Table I sets out the $\%O_2$ by volume in the carrier gas, the absolute yield, the $\%$ molar of total organic products for $C_5H_{11}ONO$, $C_5H_{11}ONO_2$ and $C_5H_{11}NO_2$ and $C_5$ Ketone + Aldehyde formed and the total absolute combined yield.

TABLE I

| Ex. No. | $O_2$ mol $dm^{-3} \times 10^4$ | $\%$ v/v | $C_5H_{11}ONO$ mol $dm^{-3} \times 10^7$ | $\%$ molar | $C_5H_{11}ONO_2$ mol $dm^{-3} \times 10^7$ | $\%$ molar |
|---|---|---|---|---|---|---|
| 1 | 0 | 0 | 3.2 | 30 | 0.14 | 1.3 |
| 2 | 1.7 | 1 | 1.3 | 14 | 3.8 | 41 |
| 3 | 9.9 | 6 | 0.07 | 0.7 | 8.9 | 85 |
| 4 | 15.4 | 9.5 | 0.13 | 1.5 | 7.2 | 86.9 |
| 5 | 26.3 | 16 | 0.35 | 3.2 | 9.5 | 86.7 |
| 6 | 31.5 | 19.5 | 0.26 | 2.4 | 9.5 | 88.6 |
| 7 | 34.8 | 22 | 0.19 | 2.3 | 7.2 | 86.8 |
| 8 | 37.8 | 23 | 0.21 | 1.7 | 10.9 | 88.2 |
| 9 | 50.2 | 31 | 0.27 | 2.7 | 8.7 | 88.2 |
| 10 | 57.4 | 36 | 0.11 | 1.1 | 9.0 | 88.5 |
| 11 | 65.8 | 41 | 0.17 | 1.6 | 9.5 | 89.3 |
| 12 | 72.5 | 45 | 0.07 | 0.6 | 9.6 | 88.9 |

| Ex. No. | $C_5H_{11}NO_2$ mol $dm^{-3} \times 10^7$ | $\%$ molar | Ketone + Aldehyde mol $dm^{-3} \times 10^7$ | $\%$ molar | Total Yield mol $dm^{-3} \times 10^7$ |
|---|---|---|---|---|---|
| 14 | 7.3 | 68.7 | not detected | | 10.64 |
| 15 | 4.0 | 43.0 | 0.2 | 2.0 | 9.3 |
| 16 | 1.2 | 11.4 | 0.3 | 2.9 | 10.47 |
| 17 | 0.66 | 8.0 | 0.3 | 3.6 | 8.29 |
| 18 | 0.60 | 5.5 | 0.51 | 4.6 | 10.83 |
| 19 | 0.47 | 4.4 | 0.49 | 4.6 | 10.72 |
| 20 | 0.38 | 4.6 | 0.52 | 6.3 | 8.29 |
| 21 | 0.47 | 3.8 | 0.78 | 6.3 | 12.36 |
| 22 | 0.28 | 2.8 | 0.62 | 6.3 | 9.87 |
| 23 | 0.26 | 2.6 | 0.80 | 7.8 | 10.17 |
| 24 | 0.25 | 2.4 | 0.71 | 6.7 | 10.63 |
| 25 | 0.20 | 1.8 | 0.94 | 8.7 | 10.81 |

We claim:

1. In a process for the production of one or more organic nitro-compounds, organic nitrates or organic nitrites comprising reacting, in the vapour phase one or more organic compounds with a nitrating agent, and recovering at least one resulting organic nitro-compound, organic nitrate or organic nitrite from the residual vapour phase, the improvement wherein radicals of the one or more organic compounds are produced for nitration by reacting hydrogen peroxide vapour and nitrogen dioxide in the presence of an acidic solid surface to produce hydroxyl radicals and reacting the hydroxyl racicals with a vapour of a reactive substrate mainly comprising the one or more organic compounds by forming a mixture containing the hydroxyl radicals and the vapour of the reactive substrate or containing hydrogen peroxide vapour and nitrogen dioxide, as hydroxyl radical precursors, in the presence of the solid surface, and the vapour of the reactive substrate whereby the radicals so produced are contacted with the nitrating agent, an additive comprising molecular oxygen being present in said vapour phase.

2. A process as claimed in claim 1 wherein the nitrating agent is nitrogen dioxide.

3. A process as claimed in claim 1 wherein the reacting step is conducted in a single stage by passing a stream comprising a mixture of hydrogen peroxide vapour, nitrogen dioxide and vapour of the one or more organic compounds through a reactor containing an acidic solid surface, the stream being in contact with the said surface, and removing from the reactor a product vapour stream comprising nitrated derivatives of the one or more organic compounds.

4. A process as claimed in claim 3 wherein a stream comprising a mixture of vapour of said one or more organic compounds and nitrogen dioxide is introduced into the reactor and hydrogen peroxide vapour is introduced into said stream within the reactor.

5. A process as claimed in claim 3 wherein the ratios of concentrations of the one or more organic compound, the nitrogen dioxide and the hydrogen peroxide are from 0.2 to $15 \times 10^{-2}$:0.5 to $50 \times 10^{-5}$:0.2 to $25 \times 10^{-6}$ mol. $dm^{-3}$.

6. A process as claimed in claim 3 operated at a rector temperature of from $0°$ C. to $200°$ C.

7. A process as claimed in claim 3 operated at a reactor pressure of from $10^3 Nm^{-2}$ to $93.3 \times 10^3 Nm^{-2}$.

8. A process as claimed in claim 3 wherein a residual proportion of the said one or more organic compounds is present in the product vapour stream together with nitrated derivatives thereof and at least a proportion of said residual quantity is removed from said derivatives.

9. A process as claimed in claim 1 wherein the acidic solid surface comprises one or more solid acids or one or more liquid or gaseous acids adsorbed on a solid surface or one or more solid acidic oxides or mixed oxides.

10. A process as claimed in claim 1 wherein the one or more organic compounds are selected from aliphatic compounds belonging to the alcohols, ketones, aldehydes, ethers or alkanes and aromatic derivatives thereof.

11. A process as claimed in claim 1 wherein the one or more organic compounds are selected from straight or branched chain alkanes containing from 1 to 10 carbon atoms.

12. A process as claimed in claim 1 wherein the reactive substrate consists of the one or more organic compounds.

13. A process as claimed in claim 1 wherein the molecular oxygen is present in from 1.75% to 50% by volume of the entire gaseous input into the process.

* * * * *